United States Patent
Gunde et al.

(10) Patent No.: US 7,566,528 B2
(45) Date of Patent: Jul. 28, 2009

(54) METHOD FOR THE IDENTIFICATION AND/OR VALIDATION OF RECEPTOR TYROSINE KINASE INHIBITORS

(75) Inventors: Tea Gunde, Zürich (CH); Catherine Berset, Windisch (CH); Alcide Barberis, Zurich (CH)

(73) Assignee: Esbatech AG, Schlieren (CH)

( * ) Notice: Subject to any disclaimer, the term of this patent is extended or adjusted under 35 U.S.C. 154(b) by 144 days.

(21) Appl. No.: 11/112,344

(22) Filed: Apr. 22, 2005

(65) Prior Publication Data
US 2005/0239049 A1 Oct. 27, 2005

Related U.S. Application Data

(63) Continuation-in-part of application No. PCT/CH03/00694, filed on Oct. 24, 2003.

(51) Int. Cl.
C12Q 1/02 (2006.01)
C12N 1/19 (2006.01)
C12N 1/38 (2006.01)
(52) U.S. Cl. .................. 435/4; 435/244; 435/254.21
(58) Field of Classification Search ............. None
See application file for complete search history.

(56) References Cited

U.S. PATENT DOCUMENTS

| 5,573,994 | A | 11/1996 | Noriyuki et al. |
| 6,051,397 | A | 4/2000 | Ullrich et al. |
| 6,433,154 | B1 | 8/2002 | Ostrander et al. |
| 2003/0182668 | A1 | 9/2003 | Bol et al. |
| 2006/0068388 | A1* | 3/2006 | Barberis et al. ........... 435/6 |

FOREIGN PATENT DOCUMENTS

WO WO 93/15201 8/1993
WO WO 2005/040413 A1 5/2005

OTHER PUBLICATIONS

Amicone et al, *The EMBO Journal*, vol. 16, pp. 495-503, 1997.*
Gunde, T. European BioPharmaceutical Review, Spring 2004, pp. 56-60.*
Kendall et al., "Inhibition of Vascular Endothelial Cell Growth Factor By An Endogenously Encoded Soluble Receptor," *Proceedings of the National Academy of Sciences of USA, National Academy of Science*, Washington, U.S., vol. 90, No. 22, Nov. 15, 1993, pp. 10705-10709.
Thiesing J. Tyler et al., "Efficacy of STI571, An ABL Tyrosine Kinase Inhibitor, In Conjunction With Other Antileukemic Agents Against BCR-ABL-Positive Cells," *Blood*, W.B. Saunders Company, Orlando, Florida, U.S., vol. 96, No. 9, Nov. 1, 2000, pp. 3195-3199.
International Search Report corresponding to International Patent Application Serial No. PCT/CH03/00694, European Patent Office, Feb. 9, 2004, 3 pages.
Weijland et al., Src regulated by C-terminal phosphorylation is monomeric. *Proc. Natl. Acad. Sci.* USA. 94: 3590-5 (1997).
Weijland et al., The purification and characterization of the catalytic domain of Src expressed in *Schizosaccharomyces pombe. Eur. J. Biochem.* 240: 756-64 (1996).

* cited by examiner

*Primary Examiner*—Jeffrey Stucker
*Assistant Examiner*—Stephen Gucker
(74) *Attorney, Agent, or Firm*—Marshall, Gerstein & Borun LLP

(57) ABSTRACT

An in vivo method for the identification and/or validation of receptor tyrosine kinase inhibitors is described. Said method is characterized by the following steps: providing host cells comprising a nucleic acid construct encoding a peptide which comprises a tyrosine kinase domain of a receptor tyrosine kinase wherein said peptide lacks a transmembrane domain or a functional fragment thereof and said tyrosine kinase activity in the cytoplasma leads to proliferation arrest, contacting said host cells with a candidate compound and identification of inhibitors of said tyrosine kinase activity by cultivation of said host cells under suitable conditions such that the modulation of the tyrosine kinase activity by the candidate compound leads to cell growth.

13 Claims, 5 Drawing Sheets

METHOD FOR THE IDENTIFICATION AND/OR VALIDATION OF RECEPTOR TYROSINE KINASE INHIBITORS

CROSS REFERENCE TO RELATED APPLICATIONS

This application is a Continuation in part application of international application no. PCT/CH03/00694 filed Oct. 24, 2003, the disclosure of which is incorporated herein by reference in its entirety.

TECHNICAL FIELD

The present application relates to a cell-based method for the identification and/or validation of inhibitors of a receptor tyrosine kinase activity.

BACKGROUND ART

Receptor tyrosine kinases (RTKs) are key regulators of intercellular communication that controls cell growth, proliferation, differentiation, survival and metabolism. About 20 different RTK families have been identified that share a similar structure, namely an extracellular binding site for ligands, a transmembrane region and an intracellular tyrosine kinase domain (1). Extracellular ligand binding induces or stabilizes receptor dimerization leading to increased RTK kinase activity. The intracellular catalytic domain displays the highest level of conservation among RTKs and includes the ATP-binding site that catalyzes receptor autophosphorylation of cytoplasmic tyrosine residues, which serve as docking sites for Src homology 2 (SH2)-and phosphotyrosine-binding (PTB) domain-containing proteins such as Grb2, Shc, Src, Cb1 or phospholipase C γ. These proteins subsequently recruit additional effectors containing SH2, SH3, PTB and pleckstrin-homology (PH) domains to the activated receptor, which results in the assembly of signaling complexes at the membrane and the activation of a cascade of intracellular biochemical signals.

The most important downstream signaling cascades activated by RTKs include the Ras-extracellular regulated kinase (ERK)-mitogen activated (MAP) kinase pathway, the phosphoinositide 3-kinase (PI 3-kinase)-Akt and the JAK/STAT pathway. The complex signaling network triggered by RTKs eventually leads either to activation or repression of various subsets of genes and thus defines the biological response to a given signal.

The activity of RTKs and their mediated cellular signaling is precisely coordinated and tightly controlled in normal cells. Deregulation of the RTK signaling system, either by stimulation through growth factor and/or through genetic alteration, result in deregulated tyrosine kinase activity. These aberrations generally result in RTKs with constitutive or strongly enhanced kinase activity and subsequent signaling capacity, which leads to malignant transformation. Therefore, they are frequently linked to human cancer and also to other hyperproliferative diseases such as psoriasis (2). The most important mechanisms leading to constitutive RTK signaling include overexpression and/or gene amplification of RTKs, genetic alterations such as deletions and mutations within the extracellular domain as well as alterations of the catalytic site, or autocrine-paracrine stimulation through aberrant growth factor loops.

For example, in many human cancers, gene amplification and/or overexpression of RTKs occurs, which might increase the response of cancer cells to normal growth factor levels. Additionally, overexpression of a specific RTK on the cell surface increases the incidence of receptor dimerization even in the absence of an activating ligand. In many cases this results in constitutive activation of the RTK leading to aberrant and uncontrolled cell proliferation and tumor formation. An important example for such a scenario is HER2, also known as ErbB2, that belongs to the epidermal growth factor (EGF) receptor family of RTKs. Overexpression of HER2 was found in various types of human cancers, especially in human breast and ovarian carcinomas (3). Most importantly, aberrantly elevated levels of HER2 correlate with more aggressive progression of disease and reduced patient survival time (4). EGFR, which was the first receptor tyrosine kinase to be molecularly cloned (5), also plays a fundamental role in tumorigenesis. EGFR is frequently overexpressed in non-small-cell lung, bladder, cervical, ovarian, kidney and pancreatic cancer and in squamous-cell carcinomas of the head and neck (6). The predominant mechanism leading to EGFR overexpression is gene amplification with up to 60 copies per cell reported in certain tumors (7). In general, elevated levels of EGFR expression are associated with high metastatic rate and increased tumor proliferation (8).

Since tyrosine kinases have been implicated in a variety of cancer indications, RTKs and the activated signaling cascades represent promising areas for the development of target-selective anticancer drugs. One approach to inhibit aberrant RTK signaling is the development of small-molecule drugs that selectively interfere with their intrinsic tyrosine kinase activity and thereby block receptor autophosphorylation and activation of downstream signal transducers (9).

Several methods have been developed to screen compound libraries in order to identify RTK-specific inhibitors, most of which utilize biochemical assays (10). One important aspect to consider for the selection of effective tyrosine kinase inhibitors is that these compounds must be able to permeate through cellular membranes and function in an intracellular environment for the necessary period of time. In addition, in order to become potential drug candidates kinase inhibitors must not show cytotoxic effects. It is therefore desirable to have a cellular system for the primary screening of compounds capable of inhibiting RTK activity. The requirements for such in vivo assays are the ability to examine a specific cellular process triggered by a defined target and a means to readily measure its output in a high-throughput screening system (HTS). The availability of an increasing number of biotechnological tools to genetically modify cells and microorganisms have allowed the development of simple read-out assays for cellular processes that can be readily applied to automated systems in HTS (11-14). Cellular screens should ideally be performed with cells of human origin, which evidently provide the most physiologically relevant model system. However, the effects of redundant processes on the measured output can be difficult to control and to distinguish from the effects that are expected to be specific for the defined target; and genetic manipulation of mammalian cells is generally problematic and time-consuming. Moreover, human cells are expensive to culture and sometimes difficult to propagate in automated systems used for HTS. Microorganisms such as yeast present a convenient alternative for measuring the activity of defined human proteins in a heterologous, yet cellular (eukaryotic) environment. In yeast cells, the function of human proteins can often be reconstituted and aspects of some human physiological processes can be recapitulated because of the high degree of conservation of basic molecular and cellular mechanisms between yeast and human cells (14-17). The fact that many human proteins function in yeast indicates that the required conformation, stability, protein-protein interaction, etc. are taking place in this eukaryotic organism.

Although there exist already methods for the isolation of receptor tyrosine kinase inhibitors, there is a need for a reliable cell-based method for the identification and/or validation of inhibitors of a receptor tyrosine kinase that permeate cell membranes and that are not cytotoxic.

DISCLOSURE OF THE INVENTION

Hence, it is a general object of the invention to provide a method for the identification and/or validation of inhibitors of a receptor tyrosine kinase activity. Said method comprises the following steps:

providing host cells comprising a nucleic acid construct encoding a peptide which comprises a tyrosine kinase domain of a receptor tyrosine kinase or a functional fragment thereof wherein said peptide lacks a transmembrane domain or a functional fragment thereof and said tyrosine kinase activity in the cytoplasma leads to proliferation arrest of said host cells, contacting said host cells with a candidate compound and identification of inhibitors of said tyrosine kinase activity by cultivation of said host cells under suitable conditions such that the modulation of the tyrosine kinase activity by the candidate compound leads to cell proliferation.

In a preferred embodiment of the present invention said nucleic acid construct encodes a peptide which comprises the entire cytoplasmic part of said receptor tyrosine kinase.

In a further preferred embodiment said peptide lacks a signal sequence and/or peptide leading to nuclear localisation of said peptide.

In a further preferred embodiment said peptide further comprises a dimerization domain or a functional fragment thereof. Said dimerization domain is preferably selected from c-Fos leucine zipper, c-Jun leucine zipper and Gcn4 leucine zipper.

In a much preferred embodiment the host cells comprise two peptides wherein the first peptide comprises a c-Fos leucine zipper and the second peptide comprises a c-Jun leucine zipper.

In another preferred embodiment said peptide comprises a sequence leading to membrane anchoring of the peptide, in particular a myristolation signal for membrane anchoring.

The tyrosine kinase activity for use in the method of the present invention can stem from any receptor tyrosine kinase. Preferred receptor tyrosin kinases are EGFR, ERBB2, ERBB3, ERBB4, INSR, IGF-1R, IRR, PDGFRα, PDGFRβ, CSF-1R, KIT/SCFR, FLK2/FLT3, VEGFR 1-3, FGFR 1-4, CCK4, TRKA, TRKB, TRKC, MET, RON, EPHA 1-8, EPHB 1-6, AXL, MER, TYRO3, TIE, TEK, RYK, DDR1, DDR2, RET, ROS, LTK, ALK, ROR1, ROR2, MUSK, AATYK, AATYK2, AATYK3, RTK 106.

In a much preferred embodiment said tyrosine kinase activity is selected from the group consisting of INSR, IGF-1R, PDGFRα, PDGFRβ, KIT/SCFR, FGFR-1, TRKA, MET, RON, EPHB2, EPHB4, AXL, TEK, RET, ROS, and /or from the group consisting of CSF-1R, FLK2/FLT3, TRKB, TRKC, EPHA 2, TIE, ALK, EGFR, ERBB2, VEGFR 1, VEGFR 2, FGFR 2-4.

In another preferred embodiment said receptor tyrosine kinase has human origin.

In another preferred embodiment said receptor tyrosine kinase has rodent origin, in particular murine origin.

In a further preferred embodiment said nucleic acid construct comprises an inducible promoter, preferably a galactose inducible promoter, which controls the expression of said peptide.

In yet another preferred embodiment said host cells are yeast cells or bacterial cells, preferably S. cerevisiae cells, more preferably S. cerevisiae cells harboring a mutation in a ABC transporter gene. Other suitable cells are cells with a mutation in the ERG6 gene and/or mutations in genes encoding phosphatases, in particular the PTP1 gene. The cells may comprise one to all of such mutations in ABC transporter genes, the ERG6 gene and/or in genes encoding phosphatases.

In yet another preferred embodiment said host cells are yeast cells or bacterial cells, preferably S. cerevisiae cells, more preferably S. cerevisiae cells harboring a mutation in one gene or any combination of genes selected from the group comprising the ABC transporter genes.

In another aspect the present invention is directed to a yeast expression vector comprising a nucleic acid construct of the present invention and a kit for the identification and/or validation of receptor tyrosine kinase inhibitors.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

The present invention provides a cell-based system for the identification and/or validation of specific inhibitors of receptor tyrosine kinases (RTKS), preferably human RTKs. In this system, host cells, preferably yeast cells, conditionally expressing defined fragments of RTKs, are enabled to grow only upon inhibition or inactivation of the protein kinase activity. Such a positive readout allows selection of specific kinase inhibitors that must also be soluble, stable and non-cytotoxic.

Figure 1A:
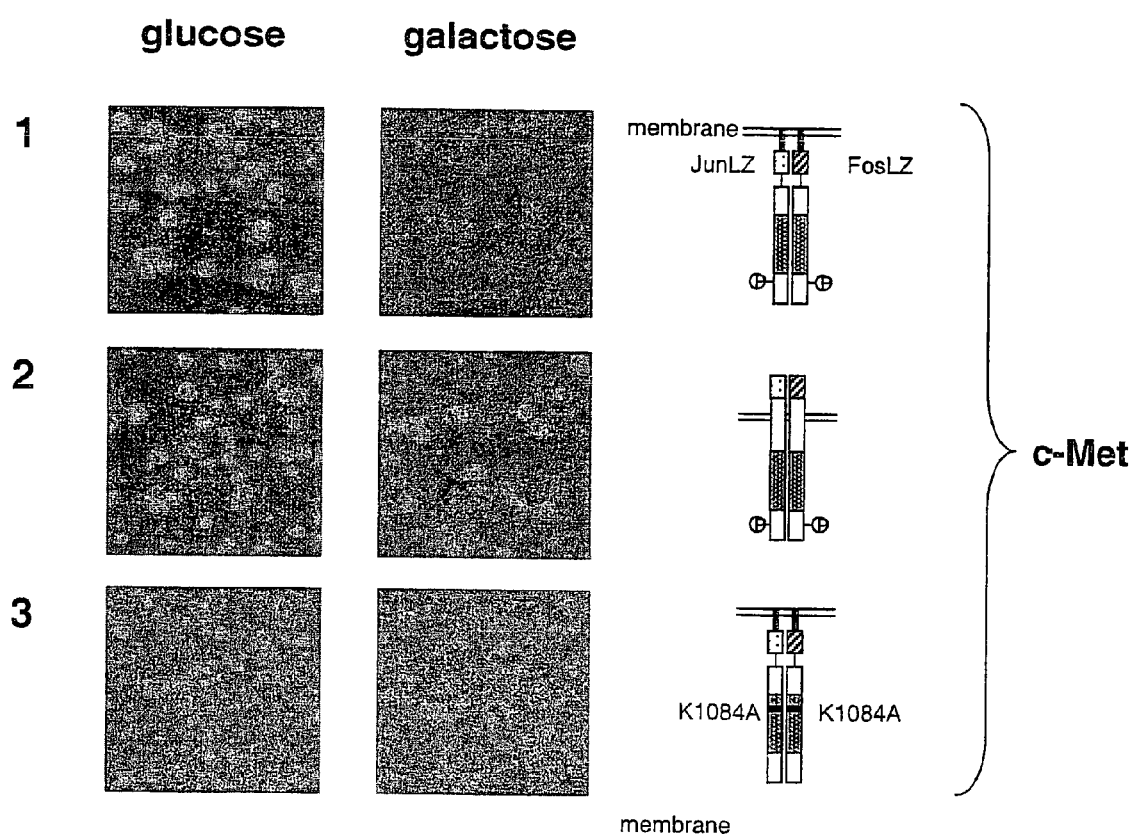
FIG. 1a shows three c-Met constructs and the effect of their expression on yeast growth.
Figure 1B:
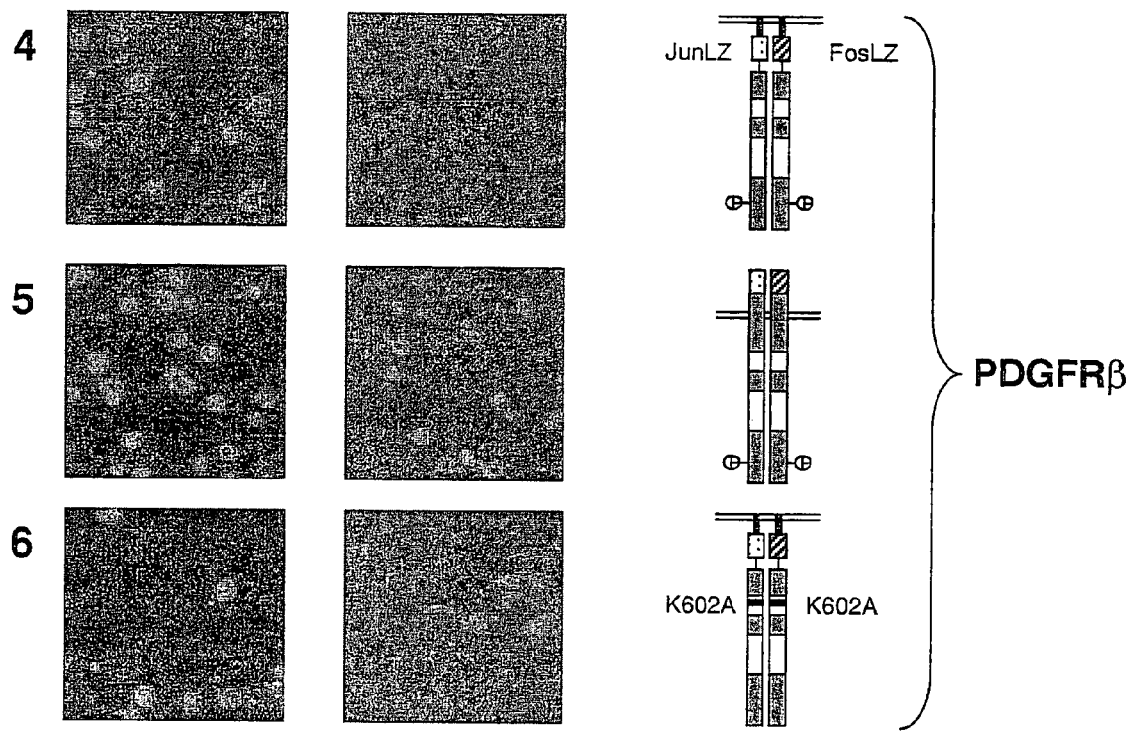
FIG. 1b shows three PDGFRβ constructs and the effect of their expression on yeast growth. Glucose=repressive conditions i.e. the peptides are not expressed and galactose=permissive conditions i.e. peptides are expressed.

In the cell-based system of the present invention, a tyrosine kinase domain of a RTK or functional fragments thereof, preferably cytoplasmic domains of RTKs or fragments thereof, are expressed in the cytoplasma of host cells either as such or as fusion peptides with protein sequences that are known to form strong dimers. Expression of these proteins in cells, preferably yeast cells, is preferably controlled by inducible promoters such as that of the GAL1 gene. Expression of dimerizing RTK derivatives significantly reduces growth of yeast cells under selective conditions (FIGS. 1a and 1b). Such growth inhibition is due to the dimerization dependent activation of the tyrosine kinase activity, since the introduction of a point mutation in the active site, which abolishes the tyrosine kinase function of RTKs; eliminates the growth inhibition effect (FIGS. 1a and 1b). Western blot analysis of cell extracts with anti-phosphotyrosine antibodies shows that the growth inhibition effect of RTKs, such as for example c-Met and PDGFRβ, correlated with its ability to catalyze tyrosine phosphorylation (FIG. 2b).

Figure 2A:
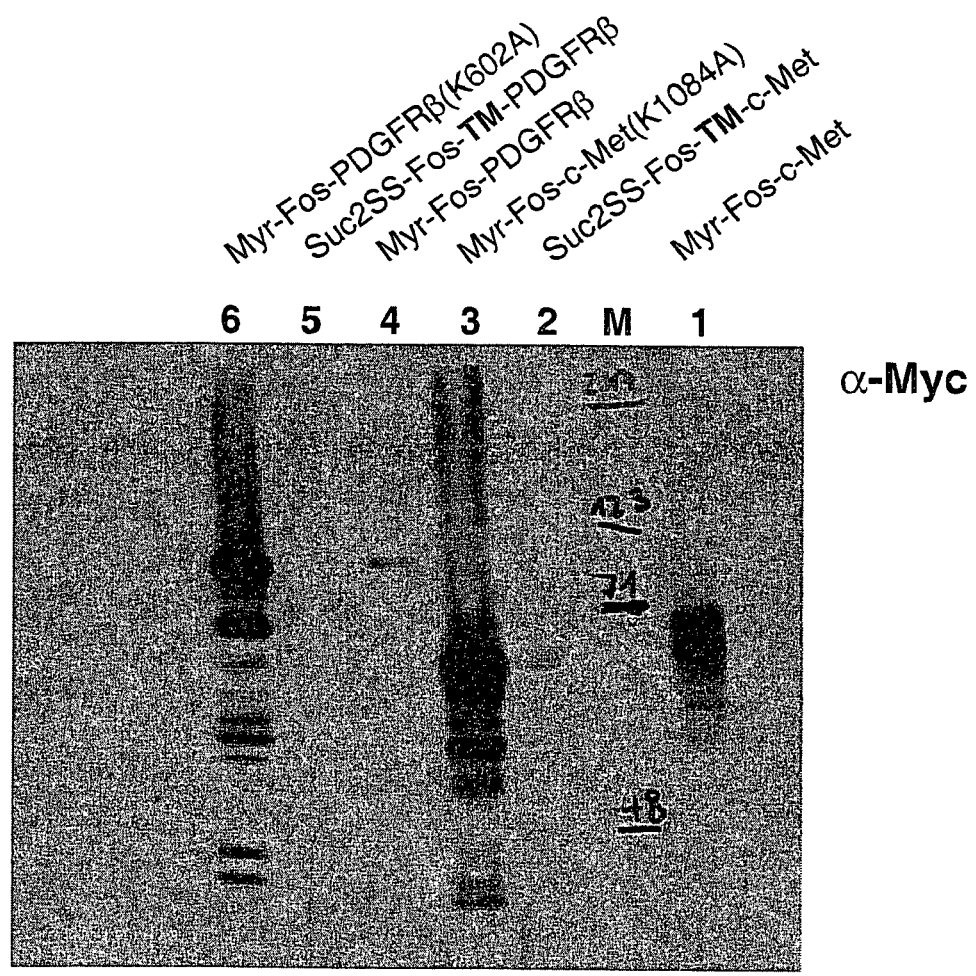
FIG. 2a shows a Western blot analysis of cell extracts with anti-myc antibodies.
Figure 2B:
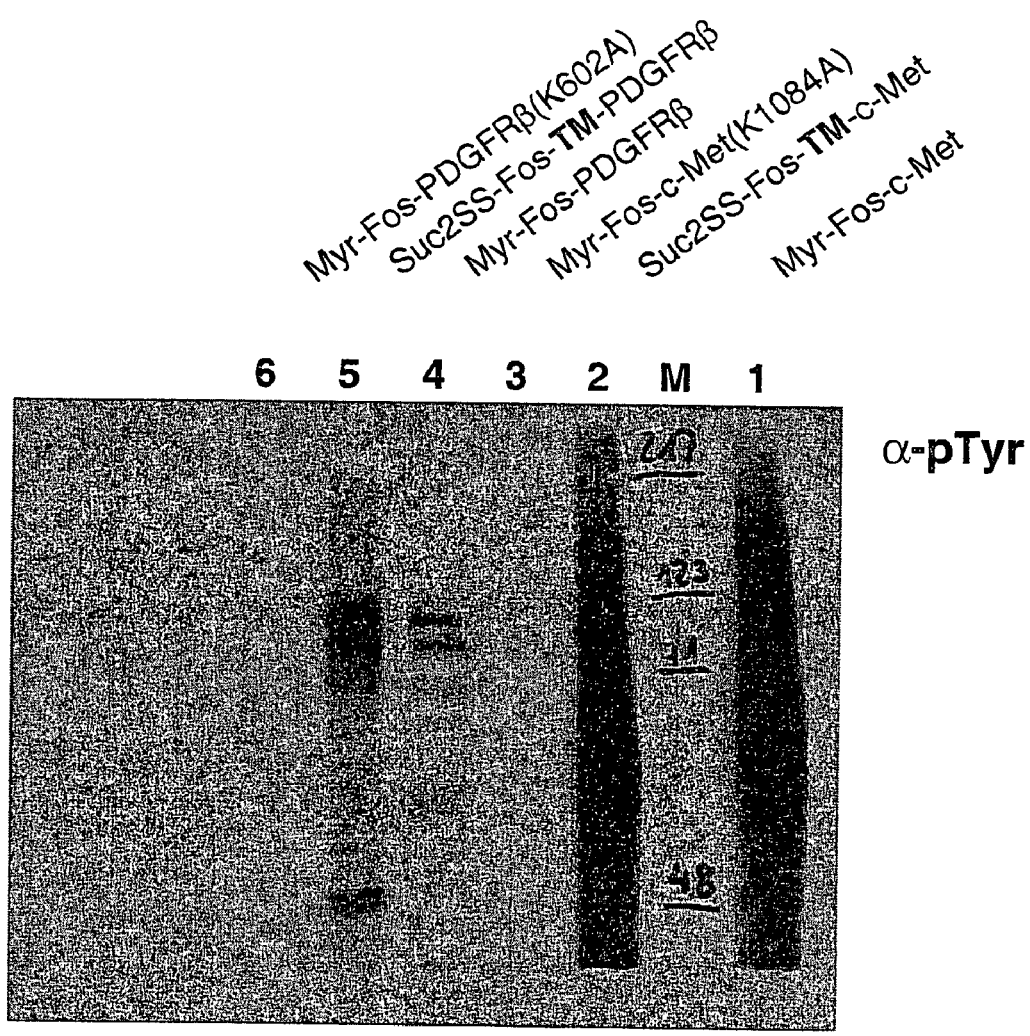
FIG. 2b shows a Western blot analysis of cell extracts with antiphosphotyrosine antibodies and FIG. 3 shows the inhibition of the Receptor Tyrosine Kinase activity of PDGFRβ by Gleevec in yeast cells.

Expression of RTK peptides that include a transmembrane domain or a functional fragment thereof, in particular a transmembrane domain of a RTK, and a signal peptide for localization of the protein N-terminus into the ER lumen and extracellular space completely abolishes the growth inhibition effect (FIGS. 1a and 1b), while it does not diminish the ability of the transmembrane RTK to catalyze tyrosine phosphorylation (FIG. 2b). Targeting active RTK cytoplasmic domains to the cytosolic part of cellular membranes is apparently not relevant for the tyrosine phosphorylation and growth inhibition effects, since no difference is observed between expression of plain RTK cytoplasmic domains and the same sequences carrying the myristolation signal for membrane anchoring (the latter one shown in FIGS. 1a, 1b and 2a).

The prior art discloses that expression of the full-length cytoplasmic tyrosine kinase c-src in S. pombe leads to cell death (18) and that expression of pp60v-src in S. cerevisiae leads to growth arrest (19). pp60v-src mutants lacking a functional N-terminal myristolation signal cause only a partial inhibition of growth arrest (19) i.e. a complete growth arrest induced by pp60v-src expression in S. cerevisiae can only be observed when pp60v-src is targeted to its natural cell compartment. The inventors of the present invention have in contrast to the prior art found that expression of a full length RTK in yeast cells does not lead to growth arrest i.e. targeting a RTK to its natural cell compartment (transmembrane localisation) in yeast cells does not lead to growth arrest.

Figure 3:
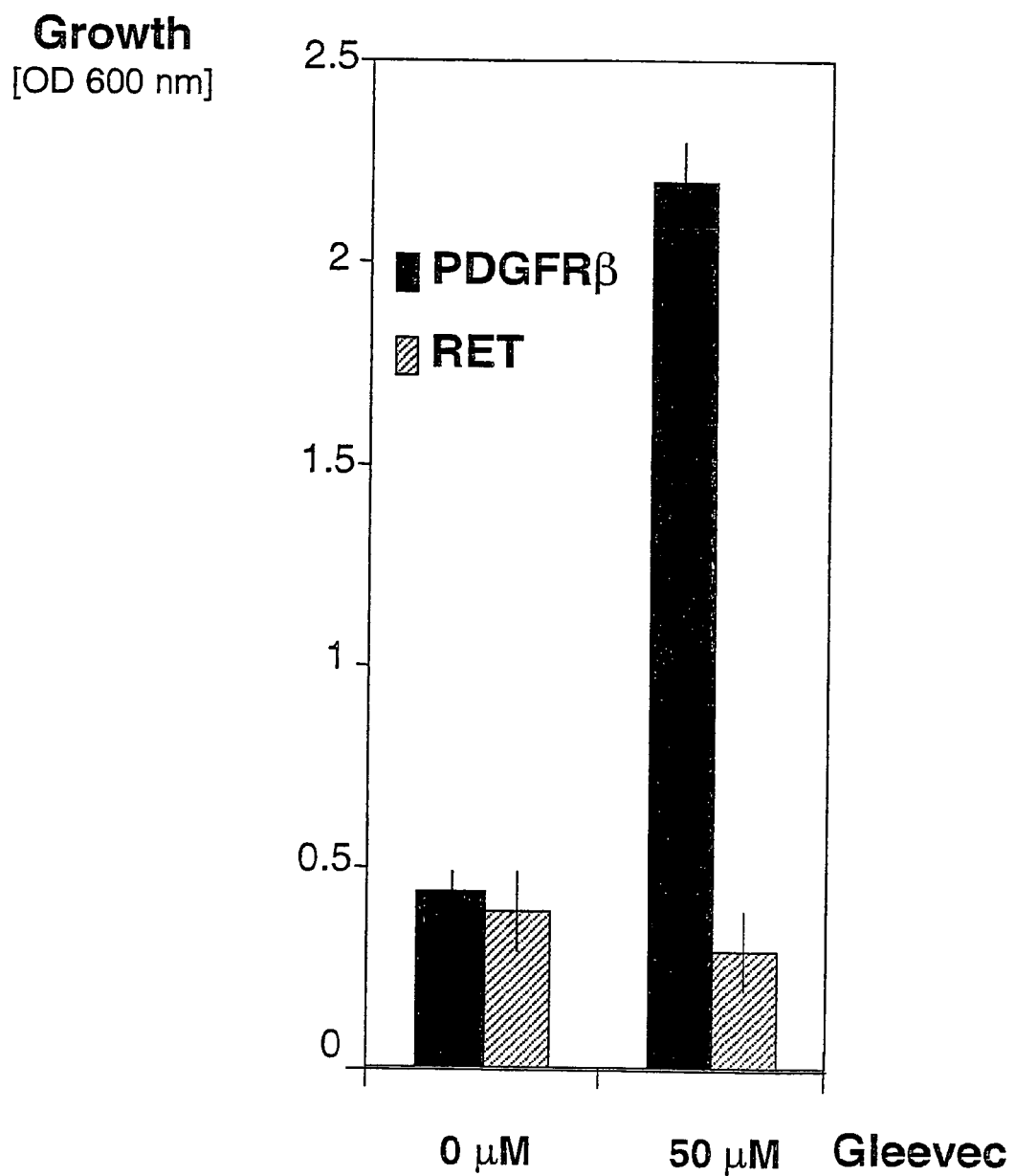

In an exemplary embodiment of the present invention, administration of the specific tyrosine kinase inhibitor imatinib mesylate (Gleevec®, Novartis) to engineered yeast cells expressing a dimerizing fragment of the RTK PDGFRβ was shown to block the dimerization-dependent kinase activity of this RTK and to restore growth under selective conditions (FIG. 3). Growth inhibition caused by a different RTK (e.g. RET), which is known to be unaffected by the specific kinase inhibitor Gleevec, was not relieved in the presence of this compound (FIG. 3).

Since bacterial and yeast cells do not have endogenous mammalian-type tyrosine kinases, this cell-based system offers the advantage of a null background for the expression of RTKs and for the screening of specific inhibitors of these membrane-bound kinases, a privileged situation that could not be obtained with mammalian cells.

A peptide of the present invention can be expressed from an extrachromosomal gene construct e.g. from an episomal vector enabling expression of the fusion protein in a host cell. The nucleic acid construct encoding the fusion peptide can be integrated into the genome of the host cell. The nucleic acid can be introduced into the cell by any transfection method leading to uptake of the nucleic acid sequence into the cell. Such methods are known to a person skilled in the art and are e.g described in Sambrook et al., Molecular Cloning: A Laboratory Manual, New York: Cold Spring Harbor Laboratory, 2001).

The construction of suitable host cells and the other molecular biological reagents for the use in the present invention e.g. fusion peptide constructs can be done using standard molecular biology techniques as described e.g. in Sambrook et al., Molecular Cloning: A Laboratory Manual, New York: Cold Spring Harbor Laboratory, 2001).

It was found that different strains (different genetic backgrounds), in particular different yeast strains, respond with different levels of growth rate reduction as a consequence of the expression of different given RTKs. Thus, it is preferred to have a broad variety of different strains available to select the best performing one for a specific RTK.

Presently preferred yeast strains for use in the screening of RTK inhibitors are:

RLY07:
MATα; ura-52; his3Δ200; leu2Δ1; trp1Δ63; lys2Δ385; Δyor1; Δsnq2; Δpdr5

RLY07Δerg6:
MATα; ura-52; his3Δ200; leu2Δ1; trp1Δ63; lys2Δ385; Δyor1; Δsnq2; Δpdr5; Δerg6

RLY09:
MATα; pdr1-3; Δura3; Δhis1; Δyor1; Δsnq2; pdr5-Δ2; Δpdr10; Δpdr11; Δycf1; pdr3-Δ2; Δpdr15; Δleu2; Δtrp1

RLY07Δptp1:
MATα; ura-52; his3Δ200; leu2Δ1; trp1Δ63; lys2Δ385; Δyor1; Δsnq2; Δpdr5; Δptp1

RLY07Δerg6Δptp1:
MATα; ura-52; his3Δ200; leu2Δ1; trp1Δ63; lys2Δ385; Δyor1; Δsnq2; Δpdr5; Δerg6; Δptp1

RLY09Δptp1:
MATα; pdr1-3; Δura3; Δhis1; Δyor1; Δsnq2; pdr5-Δ2; Δpdr10; Δpdr11; Δycf1; pdr3-Δ2; Δpdr15; Δleu2; Δtrp1; Δptp1.

The person skilled in the art is as well able to determine suitable culturing conditions allowing the detection and/or survival of the used cells. Said conditions are dependent on the used genetic constructs and the host cells.

There are at least three different categories of compounds that can be screened by a screening method of the present invention: chemical libraries, natural product libraries and combinatorial libraries. Chemical libraries consist of structural analogues of known compounds. Natural product libraries are collections of microorganism, animals, plants or marine organisms which are used to create mixtures for screening by for example fermentation and extraction of broths from soil, plant or marine microorganisms or extraction of plants or marine organisms. Combinatorial libraries are composed of large numbers of peptides, oligonucleotides or organic compounds as a mixture. They are relatively easy to prepare e.g. by traditional synthesis methods, PCR or cloning.

The invention is now further described by means of examples:

Experiment 1

The results of this experiment are shown in FIG. 1 and FIGS. 2a and 2b.

Cell growth and colony formation on glucose plates, on which expression of the RTK genes is repressed, is shown in the left row. Cell growth and colony formation on galactose plates, on which RTK gene expression is induced, is shown in the right lane. Expression of active cytoplasmic domains of the RTKs c-Met and PDGFRβ causes kinase-dependent growth inhibition of yeast cells (FIGS. 1a and 1b, lanes 1 and 4). Inactivation of the kinase activity through mutation of a conserved lysine residue (Lys=K) in the ATP-binding pockets of these RTKs suppresses the growth inhibitory effect (FIGS. 1a and 1b, lanes 3 and 6). In contrast to the isolated cytoplasmic domains of these RTKs, inclusion of the respective transmembrane domains of these proteins, in addition to a signal peptide for ER localization and secretion, caused the abolition of the inhibitory effect on cell growth (FIGS. 1a and 1b, lanes 2 and 5).

To constitutively activate c-Met and PDGFRβ, a heterologous dimerization domain was fused to the c-Met and PDGFRβ cytoplasmic domains or the c-Met and PDGFRβ longer derivatives that included the natural transmembrane domain. The c-Jun leucine zipper or the Fos leucine zipper were fused in frame to either the N-terminus of the cytoplasmic domains of c-Met (AA932-1366) and PDGFRβ (AA524-1067), or to the N-terminus of the c-Met (AA905-1366) and PDGFRβ (AA496-1067) constructs bearing the transmembrane domains. To analyze expression of the constructs in yeast cells, an HA or a Myc epitope was inserted between the fusion site of the dimerization domain and kinase domain. For the cytoplasmic constructs, membrane localization was conferred by a myristolation signal (black bar anchored at the membrane). To ensure proper secretion of the fusion proteins containing their transmembrane domains, the yeast Suc2 signal sequence (SS) was fused N-terminally of the dimerization domains.

Expression of the indicated hybrid proteins was monitored by SDS-PAGE followed by Western blotting with anti-Myc antibodies (FIG. 2a). The indicated hybrid proteins, which carry the Myc epitope for detection, the Fos leucine zipper for heterodimer formation, and the myristolation signal (Myr) for membrane anchoring, were all expressed together with similar constructs carrying the HA epitope and the partner Jun leucine zipper instead of the functionally equivalent sequences of the detected proteins. Phosphorylation of proteins (autophosphorylation of the RTKs as well as transphosphorylation of uncharacterized substrate proteins) was detected by Western blotting with antipTyr antibodies (FIG. 2b). Although c-Met and PDGFRP derivatives bearing the transmembrane domains (TM) are expressed and active to an extent that is comparable to that of the isolated cytoplasmic domains of these RTKs (compare lane 1 with 2, and lane 4 with 5 of FIG. 2b), they do not inhibit yeast proliferation. As expected, the inactivated kinase mutants did not show any tyrosine phosphorylation (FIG. 2b, lanes 3 and 6).

Experiment 2

The results of this experiment are shown in FIG. 3.

Selection of specific inhibition of Receptor Tyrosine Kinase activity in yeast. Expression of the human receptor tyrosine kinases PDGFR-β and RET in yeast causes strong retardation of cell growth, as determined by OD 600 nm light scattering measurement of both cell cultures. Addition of the kinase inhibitor imatinib mesylate (Gleevec®, Novartis), which is known to inhibit PDGFR-β but not RET, at a concentration of 50 μM in the yeast culture specifically restores growth of PDGFR-β-expressing yeast cells but not growth of cells expressing RET.

While there are shown and described presently preferred embodiments of the invention, it is to be distinctly understood that the invention is not limited thereto but may be otherwise variously embodied and practiced within the scope of the following claims.

REFERENCES

1. Ullrich and J. Schiessinger, Signal transduction by receptors with tyrosine kinase activity. Cell 61 (1990), pp. 203-212.

2. S. C. Robertson et al., RTK mutations and human syndromes when good receptors turn bad. Trends Genet 16 (2000), pp. 265-271.

3. D. J. Slamon et al., Human breast cancer: correlation of relapse and survival with amplification of the HER2/neu oncogene. Science 235 (1987), pp. 77-82.

4. S. Paik et al., Pathologic findings from the national surgical adjuvant breast and bowel project: Prognostic significance of erbB-2 protein overexpression in primary breast cancer. J. Clin. Oncol. 8 (1990), pp. 103-112.

5. Ullrich et al., Human epidermal growth factor receptor cDNA sequence and aberrant expression of the amplified gene in A431 epidermoid carcinoma cells. Nature 309 (1984), pp. 418-425.

6. W. K. Hong and A. Ullrich, The role of EGFR in solid tumors and implications for therapy. Oncol. Biother. 1 (2000), pp. 1-29.

7. T. A. Libermann et al., Amplification, enhanced expression and possible rearrangement of EGF receptor gene in primary human brain tumours of glial origin. Nature 313 (1985), pp. 144-147.

8. K. Pavelic et al., Evidence for a role of EGF receptor in the progression of human lung carcinoma. Anticancer Res. 13 (1993), pp. 1133-1138.

9. Levitzki, Protein tyrosine kinase inhibitors as novel therapeutic agents. Pharmacol. Ther. 82 (1999), pp. 231-239.

10. S. B. Noonberg and C. C. Benz, Tyrosine kinase inhibitors targeted to the epidermal growth factor receptor subfamily: Role as anticancer agents. Drugs 59 (2000), pp. 753-767.

11. R. P. Hertzberg, and A. J. Pope, High-throughput screening: new technology for the 21st century. Curr Opin Chem Biol 4 (2000), 445-451.

12. Johnston, P. A. (2002) Cellular platforms for HTS: three case studies. Drug Discov Today 7, 353-363.

13. Gonzalez, J. E., and Negulescu, P. A. (1998) Intracellular detection assays for high-throughput screening. Curr Opin Biotechnol 9, 624-631.

14. Hughes, T. R. (2002) Yeast and drug discovery. Funct Integr Genomics 2, 199-211.

15. Botstein, D., Chervitz, S. A., and Cherry, J. M. (1997) Yeast as a, model organism. Science 277, 1259-1260.

16. Munder, T., and Hinnen, A. (1999) Yeast cells as tools for target-oriented screening. Appl Microbiol Biotechnol 52, 311-320.

17. Brenner, C. (2000) A cultivated taste for yeast. Genome Biol 1, Reviews 103.

18. Superti-Furga G, Jonsson K, Courtneidge S A. (1996) A functional screen for regulators and antagonizers of heterologous protein tyrosine kinases. Nat Biotechnol 14(5):600-5.

19. Florio M, Wilson L K, Trager J B, Thorner J, Martin G S. ((1994) Aberrant protein phosphorylation at tyrosine in responsible for the growth-inhibitory action of pp60v-src expressed in the yeast Saccharomyces cerevisiae. Mol Biol Cell 5(3): 283-96.

What is claimed is:

1. A method for identifying inhibitors of a receptor tyrosine kinase activity comprising the steps of:
  A) providing S. cerevisiae host cells comprising a nucleic acid construct encoding a peptide which comprises:
    i) a myristolation signal for membrane anchoring, and
    ii) a heterologous dimerization domain or a functional fragment thereof, and
    iii) a tyrosine kinase domain of a receptor tyrosine kinase or a functional fragment thereof, wherein said peptide lacks an extracellular domain and a transmembrane domain, and wherein said host cells harbor a mutation in a ABC transporter gene;
  B) contacting said host cells with a candidate compound, and C) identifying inhibitors of said receptor tyrosine kinase activity by cultivation of said host cells under suitable conditions such that the inhibition of the receptor tyrosine kinase activity by the candidate compound leads to cell proliferation.

2. The method of claim 1, wherein said nucleic acid construct encodes a peptide which comprises the entire cytoplasmic part of said receptor tyrosine kinase.

3. The method of claim 1, wherein said dimerization domain is selected from c-Fos leucine zipper, c-Jun leucine zipper and Gcn4 leucine zipper.

4. The method of claim 1, wherein said cells comprise two peptides wherein the first peptide comprises a c-Fos leucine zipper and the second peptide comprises a c-Jun leucine zipper.

5. The method of claim 1, wherein said receptor tyrosine kinase is selected from the group consisting of EGFR, ERBB2, ERBB3, ERBB4, INSR, IGF-1R, IRR, PDGFRα, PDGFRβ, CSF-1R, KIT/SCFR, FLK2/FLT3, VEGFR 1-3, FGFR 1-4, CCK4, TRKA, TRKB, TRKC, MET, RON, EPHA 1-8, EPHB 1-6, AXL, MER, TYRO3, TIE, TEK, RYK, DDR1, DDR2, RET, ROS, LTK, ALK, ROR1, ROR2, MUSK, AATYK, AATYK2, AATYK3, RTK106.

6. The method of claim 5, wherein said receptor tyrosine kinase is selected from INSR, IGF-1R, PDGFRα, PDGFRβ, KIT/SCFR, FGFR-1, TRKA, MET, RON, EPHB2, EPHB4, AXL, TEK, RET, ROS.

7. The method of claim 5, wherein said receptor tyrosine kinase is selected from CSF-1R, FLK2/FLT3, TRKB, TRKC, EPHA 2, TIE, ALK, EGFR, ERBB2, VEGFR 1, VEGFR 2, FGFR 2-4.

8. The method of one of claim 5, wherein said receptor tyrosine kinase has human origin.

9. The method of one of claim 5, wherein said receptor tyrosine kinase has rodent origin.

10. The method of claim 1, wherein said nucleic acid construct comprises an inducible promoter.

11. The method of claim 10, wherein the inducible promoter is a galactose inducible promoter.

12. The method of claim 1, wherein said S. cerevisiae cells harbour one or more mutations selected from in one or more genes of the group consisting of the ABC transporter genes, the ERG6 gene and genes encoding phosphatases.

13. The method of claim 12, wherein the gene encoding phosphatase is the PTP1 gene.

* * * * *